United States Patent
Pfeil et al.

(10) Patent No.: US 6,708,944 B2
(45) Date of Patent: Mar. 23, 2004

(54) FLOW CONTROL SYSTEM AND VALVE FOR CONTROLLING A FLUID FLOW

(75) Inventors: Michael C. Pfeil, Dayton, OH (US); Gary C. Fulks, Spring Valley, OH (US); John E. Pozenel, Dayton, OH (US); Douglas E. Poole, Dayton, OH (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 10/042,630

(22) Filed: Jan. 9, 2002

(65) Prior Publication Data

US 2003/0127613 A1 Jul. 10, 2003

(51) Int. Cl.⁷ .................................. F16K 7/06
(52) U.S. Cl. .............................. 251/6; 251/9; 417/477.6
(58) Field of Search ........... 251/4–10; 417/477.3–477.8

(56) References Cited

U.S. PATENT DOCUMENTS

| | | | | |
|---|---|---|---|---|
| 3,016,915 A | * | 1/1962 | Moeller, Jr. ................... | 251/6 |
| 3,289,999 A | * | 12/1966 | Konzak ......................... | 251/6 |
| 3,335,753 A | * | 8/1967 | Kiser ............................ | 251/9 |
| 3,411,534 A | * | 11/1968 | Rose ............................. | 251/9 |
| 3,511,468 A | * | 5/1970 | Young .......................... | 251/6 |
| 3,927,955 A | * | 12/1975 | Spinosa et al. ............. | 417/477 |
| 4,142,845 A | * | 3/1979 | Lepp et al. ................... | 251/9 |
| 4,217,062 A | * | 8/1980 | Trp et al. .................... | 417/477 |
| 4,228,930 A | * | 10/1980 | Hogan ......................... | 417/477 |
| 5,259,587 A | * | 11/1993 | D'Alessio et al. ............ | 251/9 |
| 5,326,033 A | * | 7/1994 | Anfindsen ................... | 251/6 |

FOREIGN PATENT DOCUMENTS

| | | |
|---|---|---|
| DE | 955 750 | 1/1957 |
| DE | 199 07 109 | 9/2000 |
| GB | 2 274 326 | 7/1994 |

* cited by examiner

Primary Examiner—Paul J. Hirsch
(74) Attorney, Agent, or Firm—Scott A. McBain

(57) ABSTRACT

A flow control system and a valve for controlling a fluid flow in a flexible conduit. The valve includes a movable member movable to compressingly contact the outer surface of the flexible conduit to adjust the flow cross-sectional area of the flexible conduit. The flow control system includes the flexible conduit, the valve, and a controller. The controller is operatively connected to the movable member for controllably moving the movable member.

13 Claims, 2 Drawing Sheets

FLOW CONTROL SYSTEM AND VALVE FOR CONTROLLING A FLUID FLOW

TECHNICAL FIELD

The present invention relates generally to fluid flow, and more particularly to a flow control system and to a valve for controlling a fluid flow.

BACKGROUND OF THE INVENTION

Conventional flow control systems include servo-controlled valves for controlling a fluid flow in a conduit. Conventional valves include needle type valves and flapper type valves wherein movement of a needle or a flapper inside the conduit adjusts the flow cross-sectional area between a full flow state and a zero flow state. Some flow control applications, such as kidney dialysis machines and intravenous drug delivery systems, require all parts of the valve in contact with the fluid flow to be clean of debris or other contaminants (such as chemical or biological contaminants) prior to each use. This requires a new valve or cleaning of the needle/flapper and other fluid-contacting portions of the valve prior to each use.

What is needed is an improved flow control system and an improved valve for controlling a fluid flow.

SUMMARY OF THE INVENTION

In a first expression of an embodiment of the invention, a valve, for controlling a fluid flow in a flexible conduit, includes a stationary member and a movable member. The stationary member is adapted to support a first region of the outer surface of the flexible conduit. The movable member is movable to compressingly contact a second region of the outer surface of the flexible conduit, wherein the second region substantially opposes the first region enabling the movable member to compress the flexible conduit to adjust the flow cross-sectional area of the flexible conduit.

In a second expression of an embodiment of the invention, a flow control system includes a flexible conduit, a valve, and a controller. The valve includes a stationary member and a movable member. The stationary member supports a first region of the outer surface of the flexible conduit. The movable member is movable to compressingly contact a second region of the outer surface of the flexible conduit, wherein the second region substantially opposes the first region enabling the movable member to compress the flexible conduit to adjust the flow cross-sectional area of the flexible conduit. The controller is operatively connected to the movable member for controllably moving the movable member.

In a third expression of an embodiment of the invention, a valve, for controlling a fluid flow in a flexible conduit, includes a stationary member, a first wheel, and a second wheel. The stationary member is adapted to support a first region of the outer surface of the flexible conduit. The first wheel has a first central axis and is drivingly rotatable about the first central axis. The second wheel has a second central axis, is attached to and projects beyond the first wheel, and is freely rotatable about the second central axis. The second central axis is spaced apart from the first central axis. Driving rotation of the first wheel moves the second wheel in a substantially circular arc to compressingly contact a second region of the outer surface of the flexible conduit. The second region substantially opposes the first region enabling the second wheel to compress the flexible conduit to adjust the flow cross-sectional area of the flexible conduit.

In a fourth expression of an embodiment of the invention, a flow control system includes a flexible conduit, a valve, and a controller. The valve includes a stationary member, a first wheel, and a second wheel. The stationary member supports a first region of the outer surface of the flexible conduit. The first wheel has a first central axis and is drivingly rotatable about the first central axis. The second wheel has a second central axis, is attached to and projects beyond the first wheel, and is freely rotatable about the second central axis. The second central axis is spaced apart from the first central axis. Driving rotation of the first wheel moves the second wheel in a substantially circular arc to compressingly contact a second region of the outer surface of the flexible conduit. The second region substantially opposes the first region enabling the second wheel to compress the flexible conduit to adjust the flow cross-sectional area of the flexible conduit. The controller is operatively connected to the first wheel for drivingly rotating the first wheel about the first central axis.

In a first broader expression of an embodiment of the invention, a valve, for controlling a fluid flow in a flexible conduit having an outer surface and a flow cross-sectional area, includes a movable member movable to compressingly contact the outer surface of the flexible conduit to adjust the flow cross-sectional area of the flexible conduit.

In a second broader expression of an embodiment of the invention, a flow control system includes a flexible conduit, a valve, and a controller. The flexible conduit has an outer surface, has an inner surface for containing a fluid flow, and has a flow cross-sectional area. The valve includes a movable member movable to compressingly contact the outer surface of the flexible conduit to adjust the flow cross-sectional area of the flexible conduit. The controller is operatively connected to the movable member for controllably moving the movable member.

Several benefits and advantages are derived from one or more of the expressions of an embodiment of the invention. Having the flow cross-sectional area be adjusted by compressingly contacting an outer surface of a flexible conduit containing the fluid flow prevents the valve components from ever coming into contact with the fluid flow. Since only the flexible conduit comes into contact with the fluid flow, only the flexible conduit is replaced or cleaned in flow control applications, such as kidney dialysis machines and intravenous drug delivery systems, requiring all parts in contact with the fluid flow to be clean of debris or other contaminants (such as chemical or biological contaminants) prior to each use. The free rotation of the second wheel about the second central axis allows the second wheel, despite its circular arc motion, to compressingly contact the flexible conduit without longitudinally moving the flexible conduit as can be appreciated by those skilled in the art.

DESCRIPTION OF THE PREFERRED EMBODIMENT

Figure 1:
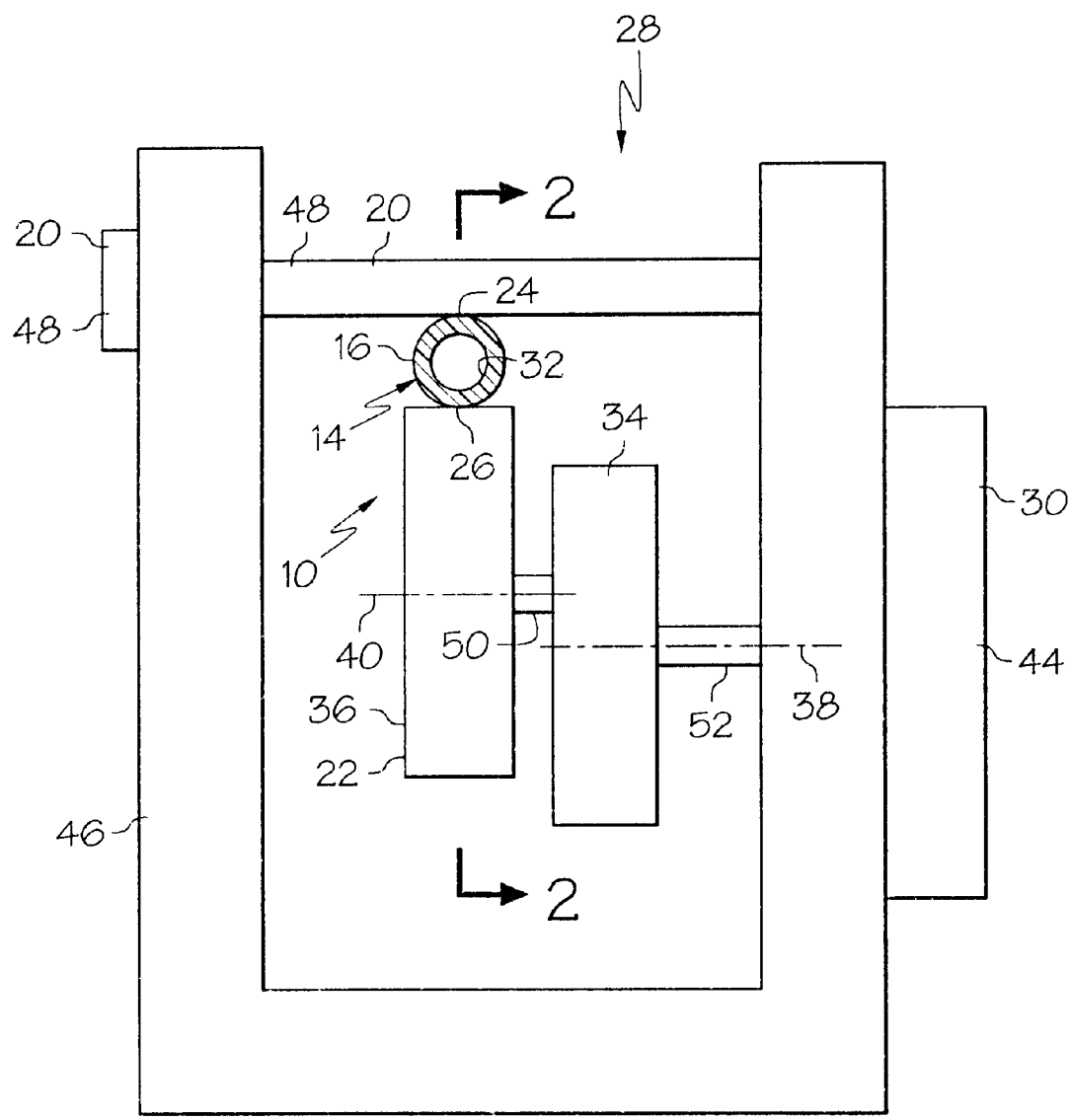
FIG. 1 is a schematic side view of an embodiment of the invention wherein the flexible conduit is shown in cross section.
Figure 2:
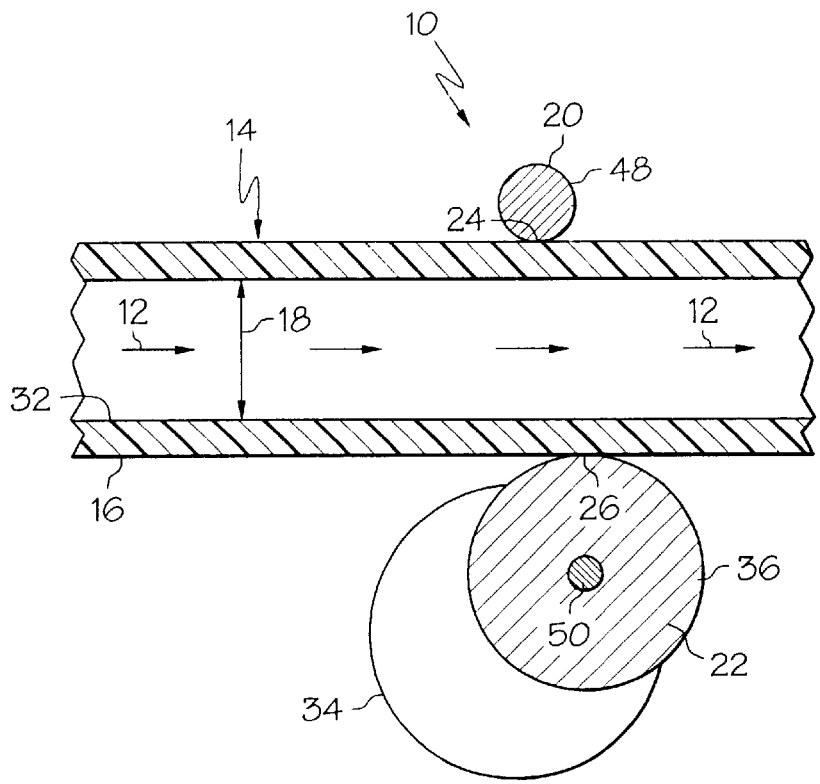
FIG. 2 is an enlarged cross-sectional view of a portion of the embodiment of FIG. 1 taken along lines 2—2 of FIG. 1 which shows the flexible conduit in a full-flow state.
Figure 3:
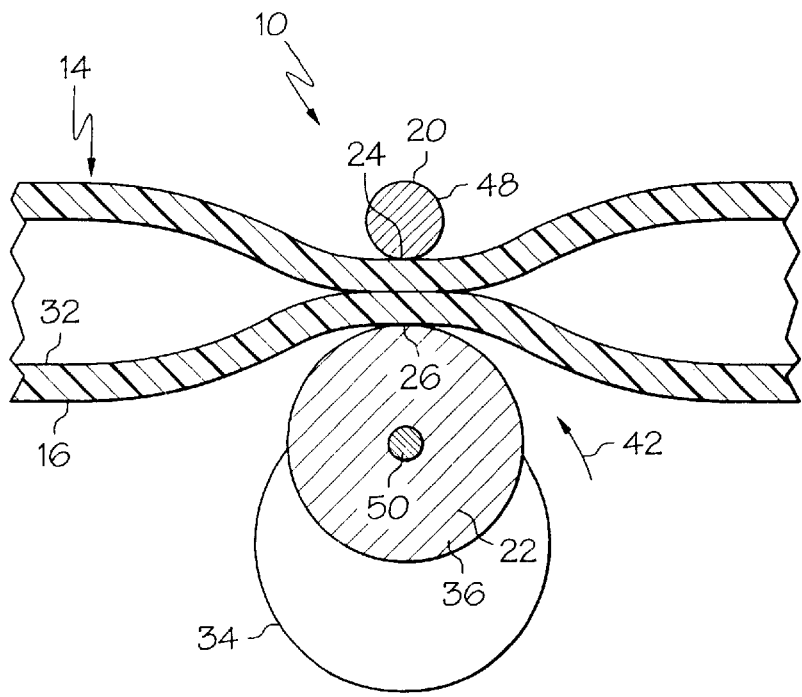
FIG. 3 is a view as in FIG. 2 but which shows the flexible conduit in a zero-flow state.

Referring now to the drawings, wherein like numerals represent like elements throughout, FIGS. 1–3 show an embodiment of the present invention. A first expression of the embodiment shown in the figures is for a valve 10, for controlling a fluid flow (represented by arrows 12 in FIG. 2) in a flexible conduit 14 having an outer surface 16 and a flow cross-sectional area (represented by a double-headed arrow 18 in FIG. 2). The valve 10 includes a stationary member 20 and a movable member 22. The stationary member 20 is adapted to support a first region 24 of the outer surface 16 of the flexible conduit 14. The movable member 22 is movable to compressingly contact a second region 26 of the outer surface 16 of the flexible conduit 14. The second region 26 substantially opposes the first region 24 enabling the movable member 22 to compress the flexible conduit 14 to adjust the flow cross-sectional area 18 of the flexible conduit 14.

In one implementation of the first expression, the fluid flow 12 comprises a gas flow. In the same or a different implementation, the fluid flow 12 comprises a liquid flow. In one application, the flexible conduit 14 is a kidney-dialysis clean-water-replacement flexible conduit. In another application, the flexible conduit 14 is an intravenous-drug-delivery flexible conduit. Other applications are left to the artisan. In one example, the movable member 22 adjusts the flow cross-sectional area 18 substantially anywhere between a substantially full-flow state (shown in FIG. 2) and a substantially zero-flow state (shown in FIG. 3). In another example, the movable member 22 adjusts the flow cross-sectional area 18 within a smaller range than a full-flow to zero-flow range.

In the first expression, the particular design and actuation of the movable member 22 is left to the artisan. Examples, not shown, of the movable member include a plunger actuated by a powered cylinder or a solenoid, an electromagnetic movable member, and a cam rotationally controlled by a servo motor. Other examples of the movable member are left to the artisan. The unique valve design including the movable member 22 shown in the figures will be described in later expressions of the embodiment of the invention.

A second expression of the embodiment shown in the figures is for a flow control system 28 including a flexible conduit 14, a valve 10, and a controller 30. The flexible conduit 14 has an outer surface 16, has an inner surface 32 for containing a fluid flow 12, and has a flow cross-sectional area 18. The valve 10 includes a stationary member 20 and a movable member 22. The stationary member 20 supports a first region 24 of the outer surface 16 of the flexible conduit 14. The movable member 22 is movable to compressingly contact a second region 26 of the outer surface 16 of the flexible conduit 14. The second region 26 substantially opposes the first region 24 enabling the movable member 22 to compress the flexible conduit 14 to adjust the flow cross-sectional area 18 of the flexible conduit 14. The controller 30 is operatively connected to the movable member 22 for controllably moving the movable member 22. The previously described implementations, applications, examples, designs, etc. of the first expression are equally applicable to the second expression. The unique valve design including the movable member 22 shown in the figures will be described in the following expressions of the embodiment of the invention.

A third expression of the embodiment shown in the figures is for a valve 10, for controlling a fluid flow 12 in a flexible conduit 14 having an outer surface 16 and a flow cross-sectional area 18. The valve 10 includes a stationary member 20, a first wheel 34, and a second wheel 36. The stationary member 20 is adapted to support a first region 24 of the outer surface 16 of the flexible conduit 14. The disposability of the stationary member 20 includes bringing the stationary member 20 to the flexible conduit 14 and/or bringing the flexible conduit 14 to the stationary member 20. The first wheel 34 has a first central axis 38 and is drivingly rotatable about the first central axis 38. The second wheel 36 has a second central axis 40, is attached to and projects beyond the first wheel 34, and is freely rotatable about the second central axis 40. The second central axis 40 is spaced apart from the first central axis 38, Driving rotation of the first wheel 34 moves the second wheel 36 in a substantially circular arc (represented by a curved arrow 42 in FIG. 3) to compressingly contact a second region 26 of the outer surface 16 of the flexible conduit 14. The second region 26 substantially opposes the first region 24 enabling the second wheel 36 to compress the flexible conduit 14 to adjust the flow cross-sectional area 18 of the flexible conduit 14.

In one implementation of the third expression, the fluid flow 12 comprises a gas flow. In the same or a different implementation, the fluid flow 12 comprises a liquid flow. In one application, the flexible conduit 14 is a kidney-dialysis clean-water-replacement flexible conduit. In another application, the flexible conduit 14 is an intravenous-drug-delivery flexible conduit. Other applications are left to the artisan. In one example, the circular arc movement of the second wheel 36 adjusts the flow cross-sectional area 18 substantially anywhere between a substantially full-flow state (shown in FIG. 2) and a substantially zero-flow state (shown in FIG. 3). In another example, the circular arc movement of the second wheel 36 adjusts the flow cross-sectional area within a smaller range than a full-flow to zero-flow range. In one design, the flexible conduit 14 proximate the first region 24 and the substantially circular arc 42 of the second wheel 36 lie substantially in a first common plane as shown in FIG. 3. In the same or a different design, the first central axis 38 and the second central axis 40 are substantially parallel and lie substantially in a second common plane. In one variation, the second common plane (represented by the plane of the paper in FIG. 1) is substantially perpendicular to the first common plane (represented by the plane of the paper in FIG. 3).

A fourth expression of the embodiment shown in the figures is for a flow control system 28 including a flexible conduit 14, a valve 10, and a controller 30. The flexible conduit 14 has an outer surface 16, has an inner surface 32 for containing a fluid flow 12, and has a flow cross-sectional area 18. The valve 10 includes a stationary member 20, a first wheel 34, and a second wheel 36. The stationary member 20 supports a first region 24 of the outer surface 16 of the flexible conduit 14. The first wheel 34 has a first central axis 38 and is drivingly rotatable about the first central axis 38. The second wheel 36 has a second central axis 40, is attached to and projects beyond the first wheel 34, and is freely rotatable about the second central axis 42. The second central axis 40 is spaced apart from the first central axis 38. Driving rotation of the first wheel 34 moves the second wheel 36 in a substantially circular arc 42 to compressingly contact a second region 26 of the outer surface 16 of the flexible conduit 14. The second region 26 substantially opposes the first region 24 enabling the second wheel 36 to compress the flexible conduit 14 to adjust the flow cross-sectional area 18 of the flexible conduit 14. The controller 30 is operatively connected to the first wheel 34 for drivingly rotating the first wheel 34 about the first central axis 38.

The previously described implementations, applications, examples, designs, variations, etc. of the third expression are equally applicable to the fourth expression. In one construction of the fourth expression, the controller 30 includes a servo motor 44. In the same or a different construction, the second wheel 36 is attached to the first wheel 34 by a stub pin 50, and a motor shaft 52 provides the operative connection of the servo motor 44 to the first wheel 34. In the same or a different construction, the valve 10 includes a housing 46, wherein the servo motor 44 is mounted to the housing 46, and wherein the stationary member 20 is a pin 48 removably attached to the housing 46. Removing the pin 48 allows easy replacement of the flexible conduit 14 as can be appreciated by those skilled in the art. Other constructions, including other stationary members, are left to the artisan.

In one choice of materials for any of the previously described expressions of the embodiment shown in the figures, the flexible conduit consists essentially of vinyl, the first wheel consists essentially of plastic, and the second wheel consists essentially of steel. In one design, the second wheel has a smooth contact surface.

As can be appreciated by the artisan, a broader first expression of the embodiment shown in the figures is for a valve 10, for controlling a fluid flow 12 in a flexible conduit 14 having an outer surface 16 and a flow cross-sectional area 18. The valve 10 includes a movable member 22 movable to compressingly contact the outer surface 16 of the flexible conduit 14 to adjust the flow cross-sectional area 18 of the flexible conduit 14. In this expression, the flexible conduit 14 is supported by one or more stationary members 20 and/or other movable members (not shown). All valve components are disposed outside the flexible conduit 14. In addition to previously described movable members and actuations, other examples (not shown) include piezoelectric material surrounding the flexible conduit, magnetorestrictive material surrounding the flexible conduit, three movable plungers disposed 120 degrees apart, and two cams disposed 180 degrees apart. Additional examples are left to the artisan and to the inventor.

As can be further appreciated by the artisan, a broader second expression of the embodiment shown in the figures is for a flow control system 28. The flow control system 28 includes a flexible conduit 14, a valve 10, and a controller 30. The flexible conduit 14 has an outer surface 16, has an inner surface 32 for containing a fluid flow 12, and has a flow cross-sectional area 18. The valve 10 includes a movable member 22 movable to compressingly contact the outer surface 16 of the flexible conduit 14 to adjust the flow cross-sectional area 18 of the flexible conduit 14. The controller 30 is operatively connected to the movable member 22 for controllably moving the movable member 22.

Several benefits and advantages are derived from one or more of the expressions of an embodiment of the invention. Having the flow cross-sectional area be adjusted by compressingly contacting an outer surface of a flexible conduit containing the fluid flow prevents the valve components from ever coming into contact with the fluid flow. Since only the flexible conduit comes into contact with the fluid flow, only the flexible conduit is replaced or cleaned in flow control applications, such as kidney dialysis machines and intravenous drug delivery systems, requiring all parts in contact with the fluid flow to be clean of debris or other contaminants (such as chemical or biological contaminants) prior to each use. The free rotation of the second wheel about the second central axis allows the second wheel, despite its circular arc motion, to compressingly contact the flexible conduit without longitudinally moving the flexible conduit as can be appreciated by those skilled in the art.

The foregoing description of several expressions of an embodiment of the invention has been presented for purposes of illustration. It is not intended to be exhaustive or to limit the invention to the precise form disclosed, and obviously many modifications and variations are possible in light of the above teaching. It is intended that the scope of the invention be defined by the claims appended hereto.

What is claimed is:

1. A valve, for controlling a fluid flow in a flexible conduit having an outer surface and a flow cross-sectional area, comprising:
   a) a stationary member having a convex surface portion adapted to support a first region of the outer surface of the flexible conduit;
   b) a substantially round first wheel having a first central axis and drivingly rotatable about the first central axis; and
   c) a substantially round second wheel having a second central axis, attached to and projecting beyond the first wheel, and freely rotatable about the second central axis, wherein the second central axis is spaced apart from the first central axis, wherein driving rotation of the first wheel moves the second wheel in a substantially circular arc to compressingly contact a second region of the outer surface of the flexible conduit, wherein the second region substantially opposes the first region enabling the second wheel to compress the flexible conduit to adjust the flow cross-sectional area of the flexible conduit, wherein the valve compresses no other region of the flexible conduit other than the second region.

2. The valve of claim 1, wherein the flexible conduit proximate the first region and the substantially circular arc of the second wheel lie substantially in a common plane.

3. The valve of claim 1, wherein the circular arc movement of the second wheel adjusts the flow cross-sectional area between a substantially full-flow state and a substantially zero-flow state.

4. The valve of claim 3, wherein the flexible conduit proximate the first region and the substantially circular arc of the second wheel lie substantially in a common plane.

5. The valve of claim 4, wherein the fluid flow comprises a gas flow.

6. The valve of claim 4, wherein the fluid flow comprises a liquid flow.

7. A flow control system comprising:
   a) a flexible conduit having an outer surface, having an inner surface for containing a fluid flow, and having a flow cross-sectional area;
   b) a valve including:
      1) a stationary member having a convex surface portion supporting a first region of the outer surface of the flexible conduit;
      2) a substantially round first wheel having a first central axis and drivingly rotatable about the first central axis; and
      3) a substantially round second wheel having a second central axis, attached to and projecting beyond the first wheel, and freely rotatable about the second central axis, wherein the second central axis is spaced apart from the first central axis, wherein driving rotation of the first wheel moves the second wheel in a substantially circular arc to compressingly contact a second region of the outer surface of the flexible conduit, wherein the second region substantially opposes the first region enabling the second wheel to compress the flexible conduit to adjust the flow cross-sectional area of the flexible conduit, and wherein the valve compresses no other region of the flexible conduit other than the second region; and c) a controller operatively connected to the first wheel for drivingly rotating the first wheel about the first central axis.

8. The flow control system of claim 7, wherein the controller includes a servo motor.

9. The flow control system of claim 8, wherein the flexible conduit proximate the first region and the substantially circular arc of the second wheel lie substantially in a common plane.

10. The flow control system of claim 9, the circular arc movement of the second wheel adjusts the flow cross-sectional area between a substantially full-flow state and a substantially zero-flow state.

11. The flow control system of claim 10, wherein the valve includes a housing, wherein the servo motor is mounted to the housing, and wherein the stationary member is a pin removably attached to the housing.

12. The flow control system of claim 11, wherein the fluid flow comprises a gas flow.

13. The flow control system of claim 11, wherein the fluid flow comprises a liquid flow.

* * * * *